(12) United States Patent
Higgins et al.

(10) Patent No.: US 6,930,223 B2
(45) Date of Patent: Aug. 16, 2005

(54) METHOD FOR ALTERING STORAGE ORGAN COMPOSITION

(75) Inventors: Thomas J. Higgins, Aranda (AU); Linda M. Tabe, Captains Flat (AU); Hartmut E. Schroeder, Hackett (AU)

(73) Assignee: Commonwealth Scientific and Industrial Research Organisation, Campbell (AU)

(*) Notice: Subject to any disclaimer, the term of this patent is extended or adjusted under 35 U.S.C. 154(b) by 41 days.

(21) Appl. No.: 09/508,979

(22) PCT Filed: Sep. 18, 1998

(86) PCT No.: PCT/AU98/00773

§ 371 (c)(1),
(2), (4) Date: May 10, 2000

(87) PCT Pub. No.: WO99/15004

PCT Pub. Date: Apr. 1, 1999

(65) Prior Publication Data

US 2003/0066101 A1 Apr. 3, 2003

(30) Foreign Application Priority Data

Sep. 19, 1997 (AU) ............................................. 9305/97

(51) Int. Cl.⁷ ............................................. C12N 15/82
(52) U.S. Cl. ...................... 800/278; 800/281; 800/284; 800/287
(58) Field of Search ................................. 800/278, 281, 800/284, 287; 435/419, 468

(56) References Cited

U.S. PATENT DOCUMENTS

| 5,850,024 A | 12/1998 | Beach et al. ................. 800/250 |
| 5,936,140 A | 8/1999 | Beach et al. ................. 800/312 |

FOREIGN PATENT DOCUMENTS

| EP | 0 255 378 B1 | 4/1994 | ........... C12N/15/82 |
| WO | 95/27068 | 10/1995 | ........... C12N/15/82 |
| WO | WO 97/35023 | 9/1997 | |
| WO | WO 97/41239 | 11/1997 | |
| WO | WO 98/13506 | 4/1998 | |

OTHER PUBLICATIONS

Altenbach et al. Accumulation of a Brazil nut albumin in seeds of transgenic canola results in enhanced levels of speed protein methionine. Plant Mol Biol. Jan. 1992; 18(2): 235–45.*

Molvig et al. Enhanced methionine levels and increased nutritive value of seeds of transgenic lupins (*Lupinus angustifolis* L.) expressing a sunflower seed albumin gene. Proc Natl Acad Sci U S A. Aug. 5, 1997; 94(16): 8393–8.*

Altenbach et al. (1992) "Accumulation of a Brazil nut albumin in seeds of transgenic canola results in enhanced levels of seed protein methionine" *Plant Molecular Biology* 18:235–245.

Blagrove et al. (1976) "Effect of Sulphur Supply on the Seed Globulin Composition of *Lupinus angustifolius*" *Aust. J. Plant Physiol* 3:176–184.

Chandler et al. (1984) "Influence of Sulfur Nutrition on Developmental Patters of Some Major Pea Seed Proteins and Their mRNAs" *Plant Physiol.* 75:651–657.

Kortt et al. (1991) "Amino acid and cDNA sequences of a methionine–rich 2S protein from sunflower seed (*Helianthus annuus* L.)" *Eur. J. Biochem.* 195:329–324.

Molvig et al. (1997) "Enhanced methionine levels and increased nutritive value of seeds of transgenic lupins (*Lupinus angustifolius* L.) expressing a sunflower seed albumin gene" *Proc. Natl. Acad. Sci.* 94:8393–8398.

Müntz et al. (1997) "Genetic Engineering of High Methionine Proteins in Grain Legumes" *Sulphur Metabolism in Higher Plants* (ed. W.J. Cram) pp. 71–86.

Saalbach et al. (1995) "The sulphur–rich Brazil nut 2S albumin is specificially formed in transgenic seeds of the grain legume *Vicia narbonensis*" *Euphytica* 85:181–192.

Townsend and Thomas (1994) "Factors Which Influence the *Agrobacterium*–mediated Transformation of Soybean" (Abstract only).

Bagga et al., "Coexpression of the Maize δ–Zein and β–Zein Genes Results in Stable Accumulation of δ–Zein in Endoplasmic Reticulum–Derived Protein Bodies Formed by δ–Zein", Plant Cell, American Society of Plant Physiologists, Rockville, MD, US, No. 9, Sep. 1, 1997, pp. 1683–1696 (Exhibit 1).

Denis et al., "Effect of sulphur levels on transgenic double–low *Brassica napus* plants expressing a seed–specific gene encoding a methionine–rich 2S albumin", Plant Breeding, vol. 115, No. 3, 1996, pp. 145–151 (Exhibit 2).

Saalbach et al., "Stable Expression of the Sulphur–rich 2S Albumin Gene in Transgenic *Vicia narbonensis* Increases the Methionine Content of Seeds", Journal of Plant Physiology, vol. 145, No. 5–6, 1995, pp. 674–681 (Exhibit 3) and.

(Continued)

Primary Examiner—Amy J. Nelson
Assistant Examiner—Cynthia Collins
(74) Attorney, Agent, or Firm—John P. White; Cooper & Dunham LLP

(57) ABSTRACT

The present invention provides a method for altering or modifying the content and/or composition of one or more metabolites in the storage organs of a plant, at least comprising the expression of a sulfur-rich protein therein. In particular, the invention provides a method of modifying the fiber content and/or fiber composition and/or starch content and/or nitrogen content and/or non-sulfur-containing amino acid composition and/or anti-nutritional protein content and/or fatty acid content and/or fatty acid composition of the storage organs of a plant. The invention clearly extends to the plants produced by the performance of the inventive method and to genetic constructs which in use produce such plant material.

59 Claims, 3 Drawing Sheets

OTHER PUBLICATIONS

Waddell et al., "Effect of over-expression on a sulphur rich 2S albumin on the sulphur metabolism of seeds in transgenic *Vicia narbonensis*", Plant Physiology (Rockville), vol. 114, No. 3 Suppl., 1997, p. 302 (Exhibit 4).

Tu, Helen M. et al. (1998) "Expression of the Brazil nut methionine-rich protein and mutants with increased methionine in transgenic potato" *Plant Molecular Biology* 37:829-838.

Keeler, Sharon J. et al (1997) "Expression of *de novo* high-lysine α-helical coiled-coil proteins may significantly increase the accumulated levels of lysine in mature seeds of transgenic tobacco plants" *Plant Molecular Biology* 34:15-29.

Marcellino, Lucilia H. et at. (1996) "Modified 2S albumins with improved tryptophan content are correctly expressed in transgenic tobacco plants" *FEBS Letters* 385: 154-158.

Tabe, L. M. et al. (1993)"Genetic engineering of grain and pasture legumes for improved nutritive value" *Genetica* 90: 181-200.

* cited by examiner

METHOD FOR ALTERING STORAGE ORGAN COMPOSITION

FIELD OF THE INVENTION

The present invention relates generally to a method for altering or modifying the composition of storage organs of a plant, at least comprising the expression of a sulfur-rich protein therein. In particular, the inventive method described herein provides altered fiber composition and/or starch content and/or nitrogen content and/or non-sulfur-containing amino acid composition and/or content of sulfur-rich anti-nutritional proteins such as protease inhibitors and/or oil content and composition of the storage organs of a plant. The invention clearly extends to the plants produced by the performance of the inventive method and to genetic constructs which are used to produce such plant material.

GENERAL

Bibliographic details of the publications numerically referred to in this specification are collected at the end of the description.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. the invention also includes all of the steps, features, compositions and compounds referred to or indicated in this specification, individually or collectively, and any and all combinations or any two or more of said steps or features.

BACKGROUND OF THE INVENTION

Chimeric genes encoding sulfur-rich proteins have been transferred to plants for the purpose of increasing he sulfur amino acid content of the seed protein. For example, the transfer of a sunflower (*Helianthus annuus*) seed albumin (SSA) gene construct to *Lupinus angustifolius* in order to enhance the sulfur amino acid content and the nutritive value of the seed protein has been reported (Molvig et al. 1997). Plants such as canola (Altenbach et al., 1992), soybean (Townsend and Thomas, 1994) and narbon bean (Saalbach et al., 1995) have been transformed with genes encoding a methionine-rich protein from Brazil nut. In these cases, enrichment of seed protein with sulfur amino acids has been reported.

It has been found that transgenic soybeans containing the Brazil nut protein (BNP) at a level approximately equal to 4% of total seed protein had reduced levels of some endogenous sulfur-rich proteins, for example a storage protein, glycinin, and the Kunitz trypsin inhibitor (Townsend and Thomas, 1994). These effects on seed storage protein composition are similar to those which accompany sulfur stress in pea and lupin seeds. In the cases of peas and lupins, seeds grown under conditions of sulfur limitation contain decreased amounts of the storage proteins that contain sulfur amino acids, and increased amounts of storage proteins with little or no sulfur amino acids (Chandler et al, 1984, Blagrove et al., 1976). In the case of the transgenic soybean, the methionine-rich BNP was made at the expense of endogenous sulfur-containing compounds.

Similarly, it has been reported that transgenic narbon beans expressing BNP do not contain increased levels of total sulfur in comparison to non-transgenic narbon beans (Muntz et al., 1997). This indicates that also in the narbon bean, a new sulfur sink causes re-routing of sulfur away from endogenous compounds. A significant part of the seed sulfur of narbon bean exists in the form of the dipeptide, γ-glutamyl cysteine (GEC). Preliminary results showed that GEC was reduced in transgenic narbon beans expressing BNP, and it has been proposed to exploit this strategy for reducing the content of the unpalatable GEC in narbon bean in order to increase its utilisation in animal feeds (Muntz et al., 1997).

Notwithstanding the development of seeds rich in sulfur-containing proteins, the nutritive value of storage organs in general and seeds in particular is not dependent exclusively upon their sulfur content and many other factors, including total protein content, oil content and composition, fibre content and content of anti-nutritional proteins such as protease inhibitors, may influence the nutritive value of storage organs intended for human and/or animal consumption. Additionally, the production of storage organs having altered oil content and composition, which oils have improved industrial utility, nutritive value, human and/or animal health properties or consumer appeal, is particularly desirable. There is currently no single method available for simultaneously improving a wide range of nutritional attributes of storage organs.

SUMMARY OF THE INVENTION

In work leading to the present invention, the inventors sought to increase the nutritive value of storage organs for human and/or animal consumption, by transferring to the genome of the plant a gene which encodes a sulfur-rich protein, such as sunflower seed albumin (SSA) containing 16% methionine and 8% cysteine (previously referred to as SFA8, Kortt et al., 1991), placed operably under the control of a promoter sequence that confers storage organ-specific expression on said gene and expressing said gene therein.

The inventors discovered that, in addition to the expected changes in sulfur-rich protein content of seeds, the overall composition of storage organs such as seeds may be altered unexpectedly such as to produce a dramatic improvement in many different and unrelated nutritive parameters. In particular, the inventors have found that this process produces an increase in the total protein content of the storage organ (exemplified herein in respect of rice, peas and chickpeas), altered storage organ fibre composition (exemplified herein in respect of lupins and peas), modified oil content and composition (exemplified herein in respect of lupins), altered storage organ starch content (exemplified herein in respect of peas) and a decrease in the content of endogenous anti-nutritional factors (exemplified herein in respect of peas and chickpeas). More than one of these changes may occur in any given plant species, and these changes may occur in addition to or instead of an expected increase in the sulfur amino acid content of seed protein.

Accordingly, one aspect of the present invention provides a method of modifying the composition of storage organs of a plant, said method comprising at least the step of expressing therein a chimeric gene comprising a genetic sequence encoding a sulfur-rich protein placed operably under the control of a promoter which is strongly expressed in developing storage organs of the plant.

The present invention also extends to a plant which has inserted into its genome a chimeric gene as broadly described above, as well as to the parts of such a plant and in particular, those storage organs which comprise at least one copy of the introduced chimeric gene.

A further aspect of the invention provides genetic constructs which comprise the chimeric genes described herein.

(i) 35S Pro-uidA-35S 3', comprising the uidA structural gene encoding the reporter enzyme β-glucuronidase placed operably under the control of the CaMV 35S promoter sequence (35S Pro) and upstream of the CaMV 35S terminator sequence (35S 3');

(ii) vicPro-ssa-vic 3', comprising the ssa structural gene encoding the sunflower seed albumin (SSA) polypeptide derived from *Helianthus annuus* placed operably under the control of the pea vicilin gene promoter sequence (vic Pro) and upstream of the vicilin gene terminator sequence (vic 3'); and (iii) 35S Pro-bar-ocs 3', comprising the *Streptomyces hygroscopicus* bar structural gene encoding the selectable marker phosphinothricin acetyltransferase (PAT) that confers resistance to glufosinate or phosphinothricin placed operably under the control of the CaMV 35S promoter sequence (35S Pro) and upstream of the *Agrobacterium tumefaciens* octopine synthase gene terminator sequence (ocs 3').

The vic Pro-ssa-vic 3' chimeric gene is flanked by EcoRI restriction sites, which may be used as a diagnostic to check for the presence of the introduced gene in plants. The genes to be introduced into the plant genome are flanked by T-DNA left-border (LB) and right-border (RD) sequences derived from the *Agrobacterium tumefaciens* Ti plasmid. Details of the gene constructions are disclosed by Molvig et al. (1997).

Figure 2:
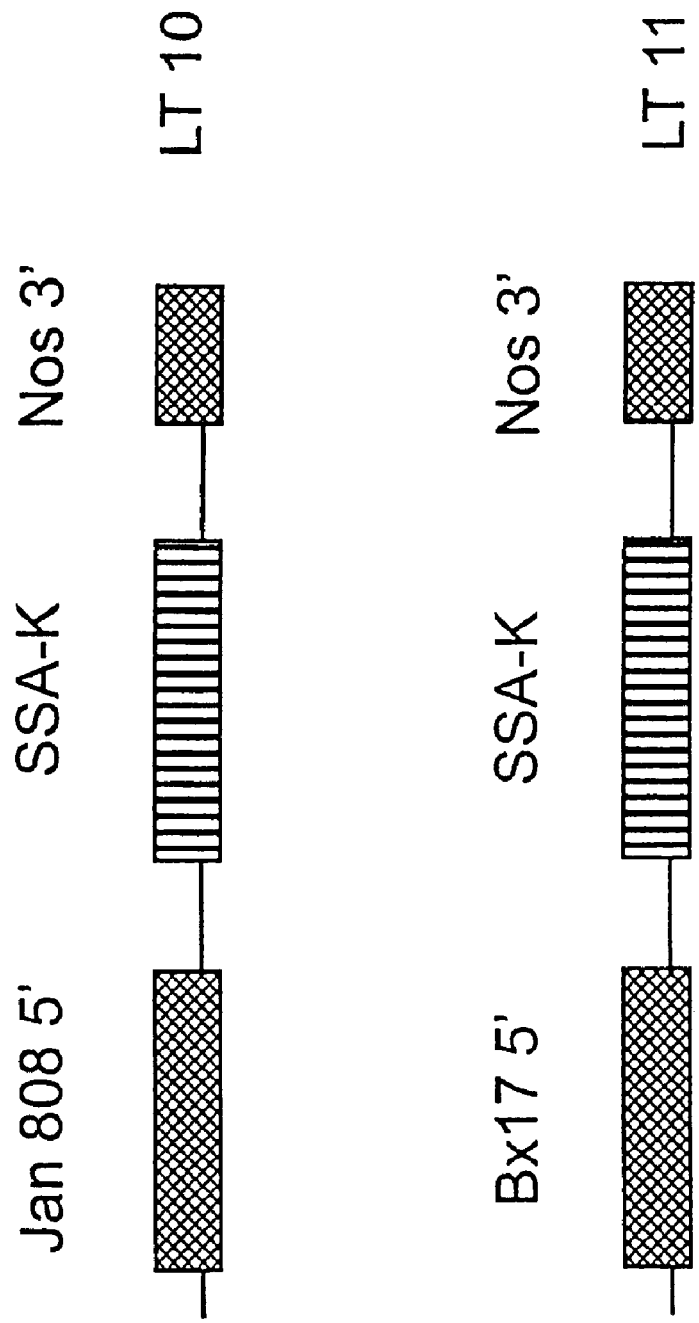

FIG. 2 is a diagrammatic representation of chimeric genes LT10 (top) and LT11 (lower) that comprises a structural gene encoding a modified SSA having a C-terminal KDEL extension (SSA-K). placed upstream of the *Agrobacterium tumefaciens* NOS transcription terminator sequence (Nos 3') and operably under the control of the wheat HMW glutenin gene promoters JAN 808 (Jan808 5' in construct LT10) or Bx17 (Bx17 5' in construct LT11). The chimeric gene LT10 or LT11 is transferred into rice in conjunction with the chimeric selectable marker gene set forth in FIG. 3.

Figure 3:
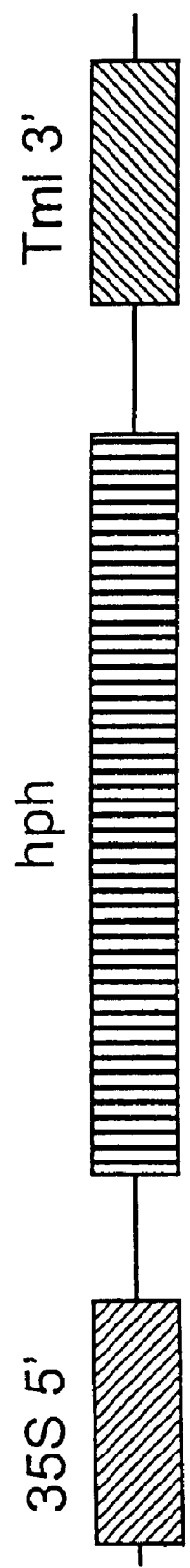

FIG. 3 is a diagrammatic representation of a chimeric selectable marker gene that comprises a structural gene derived from *Escherichia coli* encoding hygromycin phosphotransferase (hph), placed upstream of the *Agrobacterium numefaciens* tumor morphology large gene (tml) transcription terminator sequence (tml 3') and operably under the control of the CaMV 35S gene promoter. The chimeric selectable marker gene is transferred into rice in conjunction with one of the chimeric genes set forth in FIG. 2.

DETAILED DESCRIPTION OF THE PREFERRED EMBODIMENTS

Accordingly, one aspect of the present invention provides a method of modifying the content and/or composition of one or more metabolites in the storage organs of a plant, said method at least comprising the step of expressing in the storage organ of said plant a chimeric gene that comprises a genetic sequence encoding a sulfur-rich protein placed operably in connection with a promoter capable of conferring expression on said gene in the storage organ of said plant, subject to the proviso that wherein the content and/or composition of only one metabolites is modified that metabolite does not comprise the sulfurous protein content of the seed.

Accordingly, the present invention clearly encompasses a method of modifying the sulfurous protein content of the seed in conjunction with modifying the sulfurous protein content of another storage organ in the plant and/or modifying the content and/or composition of one or more other metabolites in the seed or another storage organ in the plant.

In one embodiment of the present invention exemplified herein, there is provided a method of modifying the content and/or composition of one or more metabolites in the seeds of a dicotyledonous plant, said method at least comprising the step of expressing in the storage organ of said plant a chimeric gene that comprises a genetic sequence encoding SSA placed operably in connection with the vicilin gene promoter, subject to the proviso that wherein the content and/or composition of only one metabolites is modified that metabolite does not comprise the sulfurous protein content of the seed.

In an alternative exemplified embodiment, the present invention provides a method of modifying the content and/or composition of one or more metabolites in the seeds of a monocolyledonous plant, said method at least comprising the step of expressing in the storage organ of said plant a chimeric gene that comprises a genetic sequence encoding SSA placed operably in connection with the HMW glutenin gene promoter, subject to the proviso that wherein the content and/or composition of only one metabolites is modified that metabolite does not comprise the sulfurous protein content of the seed.

The term "sulfur-rich protein" shall be taken to refer to any peptide, oligopeptide, polypeptide, protein or enzyme molecule which comprises at least about 10% sulfur-containing amino acids as a proportion of its total number of amino acids.

Sulfur-rich proteins contemplated herein include any protein that is rich in methionine and/or cysteine, such as the 2S family of proteins, including the sunflower seed albumin (SSA) and a protein from Brazil nut (hereinafter "Brazil Nut Protein" or "BNP"), amongst others. The present invention further encompasses use of the synthetic Asp1 oligopeptide which is rich in essential amino acids, including methionine.

The related term "sulfurous protein content" refers to the sulfur-rich protein content of a storage organ as a percentage or proportion of the total TCA-precipitable protein content of that storage organ.

By "sulfur-containing amino acids" is meant any naturally-occurring amino acid or synthetic analogue or derivative thereof which is capable of being incorporated into a peptide, oligopeptide, polypeptide, protein or enzyme molecule and which comprises at least one sulfur atom. Sulfur-containing amino acids include but are not limited to methionine (Met), cysteine (Cys), L-N-methylcysteine (Nmcys), L-N-methylmethonine (Nmmet), D-cysteine (Dcys), D-methionine (Dmet), D-α-methylcysteine (Dmcys), D-α-methylmethionine (Dmmet), D-N-methylcysteine (Dnmcys), D-N-methylmethionine (Dnmmet), N-(thiomethyl)glycine (Ncys), L-α-methylcysteine (Mcys) and L-α-methylmethionine (Mmet).

In a particularly preferred embodiment of the invention, the present inventors have demonstrated that, in addition to the expected increase in sulfurous protein content of the storage organ, the content and/or composition of many metabolites of the storage organs of plants may be altered by expressing therein a genetic sequence which encodes a sulfur-rich protein.

The present invention may be performed on any dicotyledonous or monocotyledonous plant species, however the advantages of the invention are particularly applicable to those plants that produce storage organs or metabolites of storage organs that are edible by animals and/or humans, for example grain crops such as wheat, oats, maize, barley, rice, sorghum, millet, oilseed rape, rye, safflower, sunflower, legumes and pulses such as lupins, soybean, peas, beans (including faba and common bean), lentils and chickpeas, and tuberous crop plants such as potatoes, sweet potato and taro. Notwithstanding, the present invention is particularly applicable to a wide range of edible and non-edible plants as exemplified herein, including *Oryza* spp. (rice), *Pisum* spp. (pea), *Cicer* spp. (chickpea) and *Lupinus* spp (lupin). The invention clearly extends in application to species of plants other than those specifically exemplified herein.

As used herein the term "storage organ" refers to any organ of a plant that stores carbon in the form of starch and/or oil and/or glucans and/or fructans, amongst others, including but not limited to seeds, tubers and specialised stems.

In the present context, the word "seed" shall be taken to refer to any plant structure which is formed by continued differentiation of the ovule of the plant, following its normal maturation point at flower opening. In general, seed may comprise storage tissue such as a haploid female gametophyte or a triploid maternally-deprived endosperm, an aleurone layer, an embryo and a seed coat. It will be known to those skilled in the art that not all mature seed comprise an endosperm and that some angiosperm seeds comprise only an embryo and seed coat, whist many gymnosperm seed comprise a female gametophyte as storage tissue (rather than an endosperm), in addition to a seed coat and an embryo.

In the present context, the word "tuber" shall be taken to refer to the storage organ of a plant species that reproduces vegetatively, albeit not necessarily exclusively by vegetative means, wherein that storage organ further comprises reproductive material by virtue of being capable of giving rise to an independent plant. Preferred tubers are those edible tubers derived from potato, sweet potato, beetroot, taro, Jerusalem artichoke, onion and garlic, amongst others.

"Specialised stems" are those stems which comprise storage organs and are derived from plant species that reproduce vegetatively, albeit not necessarily exclusively by vegetative means, wherein that storage organ further comprises reproductive material by virtue of being capable of giving rise to an independent plant, such as sugar cane and other plants capable of being propagated by cuttings.

In the context of the present invention, it is particularly preferred that the storage organ is a seed.

As used herein, a "metabolite" includes any product, bi-product or intermediate of the metabolism of a storage organ of a plant, including but not limited to amino acids, oils (i.e. fatty acids), protein, sulfurous protein, non-sulfurous protein, starch, soluble and/or insoluble non-starch polysaccharide (NSP), fibre and endogenous anti-nutritional factors, amongst others.

Anti-nutritional factors include any metabolites or constituents of a storage organ of a plant which inhibit, prevent or reduce the nutritional value of the storage organ to humans or animals and/or which act as anti-feedants and/or which prevent the breakdown of nutritional units (i.e. proteins, starch, fatty acids, etc) into smaller units during digestion. Anti-nutritional factors may be enzymes, peptides or small molecules, amongst others. Exemplary anti-nutritional factors include enzymes and peptides that inhibit the action of proteases localised in the gut of humans and/or animals, such as trypsin inhibitor, chymotrypsin inhibitor and papain inhibitors, as well as soluble NSP, lectins and non-protein amino acid derivatives containing sulfur, amongst others.

Endogenous anti-nutritional factors are those antnutritional factors that are produced by the plant and are at least present in the storage organ of the plant.

By "modifying the content and/or composition of one or more metabolites" is meant that the total steady-state level of one or more metabolites is increased or decreased as measured by art-recognised methods and/or the steady-state level of one or more constituents that comprise the total level of the metabolite is increased or decreased, including the elimination of certain constituents or metabolites to undetectable levels and/or the appearance of new constituents or metabolites.

Preferably, the metabolite which is modified by the inventive method described herein is one or more of the metabolites selected from the list comprising amino acid composition, fatty acid composition, fatty acid content, total TCA-precipitable protein content, TCA-precipitable non-sulfurous protein content, starch content, fibre composition and anti-nutritional factor content.

In a particularly preferred embodiment, the present invention provides for a modification to the total protein content of seeds and/or the fatty acid content of seeds and/or the fatty acid composition of seeds and/or the starch content of seeds and/or the fibre composition of seeds and/or the quality of seeds and/or the content of soluble NSP content and/or protease inhibitors in seeds.

Even more preferably, the present invention provides for one or more modifications to the metabolites in the seeds of monocotyledonous or dicotyledonous plants selected from the list comprising:

(i) increased total protein content;
(ii) modified amino acid composition;
(iii) modified fibre content;
(iv) altered fibre quality;
(v) reduced seed starch content;
(vi) increased or decreased total fatty acid content;
(vii) modified fatty acid composition; and
(viii) reduced protease inhibitor content.

Protein content of seeds as determined by total nitrogen content or TCA-precipitable nitrogen content may be increased by at least about 10% compared to the seeds derived from wild-type non-transformed lines of plants which are otherwise isogenic to the transformed lines expressing the introduced chimeric gene. Preferably, the total protein content of seeds is increased by at least about 20%, more preferably at least about 25%, even more preferably at least about 40% and still more preferably at least about 50% compared to the total protein content of the seeds of non-transformed otherwise isogenic lines.

As exemplified herein, the total amino acid composition of seeds (i.e. both free amino acids and amino acids incorporated into protein) which express the introduced chimeric gene is not accompanied by a mere increase in the level of sulfur-containing amino acids and increases of at least about 8–10% in the steady-state levels of all commonly naturally-occurring amino acids may be observed in such plants. Additionally, changes in amino acid composition of transformed plants which express the introduced chimeric gene are not uniform. Accordingly, the modified amino acid composition of plant storage organs which is achieved by the performance of the inventive method is in addition to any modification to sulfur-containing amino acid content that may be expected by expressing a sulfur-rich protein in a plant storage organ.

Fibre content may be determined by comparing the relative amounts of total dietary fibre [i.e. total (i.e. soluble plus insoluble) non-starch polysaccharide (NSP) plus total lignin content] in the storage organs of plants that express the introduced chimeric gene to the total dietary fibre content of the storage organs of non-transformed otherwise isogenic plant lines. Preferably, total fibre content varies by at least about 5–10%, more preferably by at least about 10–20% and even more preferably by at least about 20–30% through the performance of the invention described herein, as exemplified herein, fibre content may be increased or decreased in the seeds of plants.

Fibre composition way be determined by comparing the relative amounts of soluble NSP, insoluble NSP, total NSP and lignin in the storage organs that express the introduced chimeric gene, to the amounts of these fibre constituents in the storage organs of non-transformed otherwise isogenic plant lines.

Preferably, starch content is reduced by at least about 10%, more preferably by at least about 20%, even more preferably at least about 30% compared to the total starch content of the storage organs of non-transformed otherwise isogenic plant lines, as determined by any art-recognised method for determining the starch content of seeds (eg. enzymic digestion of starch to glucose and assay of glucose content).

The total fatty acid content of storage organs and in particular, the total fatty acid content of seeds, may be increased or decreased by at least about 5–10%, more preferably at least about 10–20%, even more preferably by at least about 25% compared to the total oil content of the storage organs of non-transformed otherwise isogenic plant lines. As exemplified herein, total fatty acid content of seeds may be increased, as is the case for lupins or decreased as is the case for peas.

Modified oil fatty acid composition preferably involves modifications to saturated fatty acids and/or unsaturated fatty acids.

Preferred saturated fatty acids the composition of which is modified by the performance of the present invention include one or more of the following: myristic acid, palmitic acid, stearic acid, arachidic acid, gadoleic acid, behenic acid and lignoceric acid. More preferably, the level of ore or more of the saturated fatty acids, myristic acid, stearic acid, gadoleic acid, behenic acid and lignoceric acid is modified by the performance of the inventive method. Even more preferably, the level of stearic acid and/or behenic acid and/or lignoceric acid is modified. In a still more preferred embodiment, the level of stearic acid is modified by the performance of the inventive method.

Preferred unsaturated fatty acids the composition of which is modified by the performance of the present invention include one or more of the following: oleic acid, linoleic acid, linolenic acid and erucic acid. Preferably, the level of linolenic acid and/or erucic acid and more preferably the level of erucic acid is modified by the performance of the inventive method.

Preferably, the content of any one fatty acid in the storage organ of a transformed plant expressing the chimeric gene is modified (i.e. increased or decreased) by at least 5%, more preferably at least about 10%, even more preferably by at least about 20% as a proportion of the total fatty acid content of the storage organ, compared to the amount of that fatty acid expressed as a proportion of the total fatty acid content derived from the storage organ of a non-transformed otherwise isogenic plant.

Preferably, the endogenous protease inhibitor content which is reduced is an endogenous sulfur-rich protease inhibitor.

In a particularly preferred embodiment, the levels of the trypsin inhibitor and chymotrypsin inhibitor are reduced in the seeds of plants which express the introduced chimeric gene therein.

The level of an endogenous protease inhibitor in the storage organ of a plant expressing the introduced chimeric gene may be determined by any art-recognised method, such as the ability of a quantifiable amount of protein derived from said storage organ to inhibit a specific amount of the protease in respect of which the inhibitor is active.

Preferably, the level of an endogenous protease inhibitor in the storage organ of a plant expressing the introduced chimeric gene is reduced by at least about 20% more preferably by at least about 30%. even more preferably by at least about 50% and still even more preferably by at least about 60%, of the inhibition of the protease which is achievable under identical assay conditions using tissue derived from the storage organs of non-transformed otherwise isogenic plants.

The word "expression" as used herein shall be taken in its widest context to refer to the transcription of a particular genetic sequence to produce sense or antisense mRNA or the translation of a sense mRNA molecule to produce a peptide, polypeptide, oligopeptide, protein or enzyme molecule. In the case of expression comprising the production of a sense mRNA transcript, the word "expression" may also be consumed to indicate the combination of transcription and translation processes, with or without subsequent post-translational events which modify the biological activity, cellular or sub-cellular localization, turnover or steady-state level of the peptide, polypeptide, oligopeptide, protein or enzyme molecule encoded by the genetic sequence.

Preferably, the chimeric gene is expressed strongly in the storage organ of the plant. By "strong expression" is meant that the chimeric gene is expressed sufficient for the steady-state level of mRNA encoded by the structural gene region of the chimeric gene or protein encoded therefor to comprise at least about 1%, preferably at least about 5% and more preferably at least about 5–10% of the total TCA-precipitable protein of the cell in which the chimeric gene is expressed, as determined by any art-recognised method.

The level of expression of a particular gene may be determined by polymerase chain reaction (PCR) following reverse transcription of an mRNA template molecule, essentially as described by McPherson et al. (1991). Alternatively, the expression level of a genetic sequence may be determined by northern hybridisation analysis or dot-blot hybridisation analysis or in situ hybridisation analysis or similar technique, wherein mRNA is transferred to a membrane support and hybridised to a "probe" molecule which comprises a nucleotide sequence complementary to the nucleotide sequence of the mRNA transcript encoded by the gene-of-interest, labelled with a suitable reporter molecule such as a radioactively-labelled dNTP (eg $[\alpha\text{-}^{32}P]dCTP$ or $[\alpha\text{-}^{35}S]dCTP$) or biotinylated dNTP, amongst others.

Expression of the gene-of-interest may then be determined by detecting the appearance of a signal produced by the reporter molecule bound lo the hybridised probe molecule. Alternatively, the rate of transcription of a particular gene may be determined by nuclear run-on and/or nuclear run-off experiments, wherein nuclei are isolated from a particular cell or tissue and the rate of incorporation of rNTPs into specific mRNA molecules is determined. Alternatively, the expression of the gene-of-interest may be determined by RNase protection assay, wherein a labelled RNA probe or "riboprobe" which is complementary to the nucleotide sequence of mRNA encoded by said gene-of-interest is annealed to said mRNA for a time and under conditions sufficient for a double-stranded mRNA molecule to form, after which time the sample is subjected to digestion by RNase to remove single-stranded RNA molecules and in particular, to remove excess unhybridised riboprobe. Such approaches are described in detail by Sambrook et al. (1989) and Ausubel (1987).

Those skilled in the art will also be aware of various immunological and enzymatic methods for detecting the level of expression of a particular gene at the protein level, for example using rocket immunoelectrophoresis, ELISA, radioimmunoassay and western blot immunoelectrophoresis techniques, amongst others.

Reference herein to a "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences);or (ii) mRNA or cDNA corresponding to the coding regions (i.e. exons) and 5'- and 3'-untranslated sequences of the gene.

The term "gene" is also used to describe synthetic or fusion molecules encoding all or part of a functional product.

In the context of the present invention, the term "chimeric gene" shall be taken to refer to any non-naturally occurring gene which comprises two or more linked genetic sequences derived from different biological sources. In one example, a chimeric gene may comprise a structural coding region derived from one biological source operably connected to a promoter sequence and/or a transcription termination sequence derived from different biological source(s).

Genetic sequences include any polymers of naturally-occurring deoxyribonucleotides and ribonucleotides and synthetic analogues and derivatives thereof. Particularly preferred genetic sequences comprise DNA and/or RNA, including single-stranded and double-stranded forms of DNA and RNA.

Preferred chimeric genes for use in the present invention at least comprise structural gene regions or protein-encoding regions that encode sulfur-rich proteins and these may be derived from naturally-occurring genes or derived using standard recombinant techniques. Particularly preferred structural gene regions include genetic sequences encoding sunflower seed albumin (SSA) or BNP, amongst others.

The present invention clearly extends to the use of structural gene regions which comprise homologues, analogues, fragments and derivatives of the SSA and BNP structural genes and other structural gene regions which encode sulfur-rich polypeptides, irrespective of whether such genetic sequences are naturally-occurring or non-naturally occurring genetic sequences.

In a particularly preferred embodiment, the structural gene region encoding the sulfur-rich protein is modified such that the polypeptide product of the modified structural gene includes the amino acid motif Lys-Asp-Glu-Leu (i.e. KDEL motif), preferably at the C-terminal end of the sulfur-protein-encoding region to facilitate targeting of the protein.

"Analogues" of a structural gene encoding a sulfur-rich protein are nucleic acid molecules which are substantially the same as the structural gene or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a structural gene encoding a sulfur-rich protein are nucleic acid molecules which contain significant sequence identity to said structural gene or a part thereof. Generally the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

Reference herein to a "promoter" is to be taken in its broadest context and includes the transcriptional regulatory sequences of a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner.

In the present context, the term "promoter" is also used to describe a synthetic or fusion molecule, or derivative which confers, activates or enhances expression of said sense molecule in a cell. Preferred promoters may contain additional copies of one or more specific regulatory elements, to further enhance expression and/or to alter the spatial expression and/or temporal expression of a nucleic acid molecule to which it is operably connected For example, copper-responsive regulatory elements may be placed adjacent to a heterologous promoter sequence driving expression of a nucleic acid molecule to confer copper inducible expression thereon.

In the context of the present invention, the term "promoter" includes those transcriptional regulatory sequences which are at least capable of conferring strong expression of the chimeric gene in the storage organ, in particular the seeds, of a plant.

Placing a nucleic acid molecule under the regulatory control of a promoter sequence means positioning said molecule such that expression is controlled by the promoter sequence. A promoter is usually, but not necessarily, positioned upstream or 5' of a nucleic acid molecule which it regulates. Furthermore, the regulatory elements comprising a promoter are usually positioned within 2 kb of the start site of transcription of the chimeric gene that encodes the sulfur-rich protein. In the construction of chimeric genes comprising heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include promoters derived from the genes of viruses, yeasts, moulds, bacteria, insects, birds, mammals and plants which are capable of functioning at least in the storage organs of a plant or the cells and tissues comprising same, in particular the maternally-derived endosperm and/or aleurone layer of the seed. The promoter may regulate the expression of the genetic sequence encoding the sulfur-rich protein constitutively or differentially, with respect to the developmental stage at which expression occurs, or in response to external stimuli such as physiological stresses, pathogens, or metal ions, amongst others.

Promoters suitable for use according to this embodiment are further capable of functioning in cells derived from both monocotyledonous and dicoyledonous plants, including broad acre crop plants or horticultural crop plants.

Examples of promoters useful in performing this embodiment include the CaMV 35S promoter, nopaline synthase Base (NOS) promoter, octopine synthase (OCS) promoter, ADP-glucose pyrophosphorylase gene promoter, patatin gene promoter, starch synthase gene promoter, napin seed-specific promoter, vicilin gene promoter, legumin gene promoter, phaseolin gene promoter, phytohemagglutinin gene promoter, rice glutelin (e.g. Glut B1) gene promoter, wheat high molecular weight (HMW) glutenin gene promoter (eg the Bx17 promoter or the JAN808 promoter, amongst others) and the like. In addition to the specific promoters identified herein, cellular promoters for so-called housekeeping genes are useful.

In a particularly preferred embodiment of the invention, the promoter used in conferring expression on the chimeric gene is the vicilin gene promoter derived from peas in the case of dicotyledonous plant species or the HMW glutenin gene promoter (Bx17 or JAN808) derived from *Triticum aestivum* in the case of monocotyledonous plant species. Other promoters are not excluded, the only requirement being that they are capable of conferring expression on the chimeric gene at a high level at least in the storage organs of the plant and particularly in the seeds.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, axis and/or plants.

Examples of terminators particularly suitable for use in the genetic constructs of the present invention include the nopaline synthase (NOS) gene terminator of *Agrobacterium tumefaciens*, the tumor morphology large (tml) gene terminator of *Agrobacterium tumefaciens*, the terminator of the Cauliflower mosaic virus (CaMV) 35S gene, the ADP-glucose pyrophosphorylase gene terminator (t3'bt2) derived from *Oryza saliva*, the zein gene terminator from *Zea mays*, the HMW glutenin gene terminator derived from *Triticum aestivum* and the pea vicilin gene terminator derived from *Pisum sativum*, amongst others.

Those skilled in the art will be aware of additional promoter sequences and terminator sequences which may be suitable for use in performing the invention. Such sequences may readily be used without any undue experimentation.

In one particularly preferred embodiment of the present invention exemplified herein, there is provided a method of modifying the amino acid composition or protein content of seeds of a chickpea plant, preferably *Cicer arietinum*, and/or a pea plant, preferably *Pisum sativum*, and/or a rice plant, preferably *Oryza sativa*, said method at least comprising the step of expressing in the seeds of said plant a chimeric gene that comprises a genetic sequence encoding SSA placed operably in connection with the vicilin gene promoter and upstream of the vicilin gene terminator sequence.

In a further particularly preferred embodiment, the invention provides a method of decreasing the fibre content (and/or altering fibre quality) of seeds of a lupin plant, preferably a *Lupinus angustifolius* plant, said method at least comprising the step of expressing in the seeds of said plant a chimeric gene that comprises a genetic sequence encoding SSA placed operably in connection with the vicilin gene promoter and upstream of the vicilin gene terminator sequence.

In a further particularly preferred embodiment, the invention provides a method of decreasing the content of anti-nutritional factors in seeds of a lupini plant, preferably a *Lupinus angustifolius* and/or a chickpea plant, preferably *Cicer arietinum* and/or a pea plant, preferably a *Pisum sativum* plant, said method at least comprising the step of expressing in the seeds of said plant a chimeric gene that comprises a genetic sequence encoding SSA placed operably in connection with the vicilin gene promoter and upstream of the vicilin gene terminator sequence.

In a further particularly preferred embodiment, the invention provides a method of altering the oil content and/or composition of seeds of a lupin plant, preferably a *Lupinus angustifolius* plant and/or a pea plant, preferably a *Pisum sativum* plant, said method at least comprising the step of expressing in the seeds of said plant a chimeric gene that comprises a genetic sequence encoding SSA placed operably in connection with the vicilin gene promoter and upstream of the vicilin gene terminator sequence.

In a further particularly preferred embodiment, the invention provides a method of altering the starch content and/or composition of the seeds of pea plants, preferably *Pisum sativum* plants, said method at least comprising the step of expressing in the seeds of said plant a chimeric gene that comprises a genetic sequence encoding SSA placed operably in connection with the vicilin gene promoter and upstream of the vicilin gene terminator sequence.

These effects could be achieved either by inserting into the genome all SSA gene solus or alternatively, a genetic construct which comprises the SSA gene in combination with one or more additional genes, for example one or more other genes encoding sulfur-rich proteins, or one or more selectable marker genes to facilitate the selection of transformed cells.

In yet a further embodiment of the invention, the subject method comprises the additional first steps of:
(i) introducing the chimeric gene into a plant cell, tissue, organ or whole organism; and
(ii) regenerating an intact plant therefrom.

As will be known to those skilled in the art, the step of transforming the cell, tissue, organ or organism with the chimeric gene may be facilitated by placing the chimeric gene within a genetic construct.

The nucleic acid molecule or a genetic construct comprising same may be introduced into a cell using any known method for the transfection or transformation of said cell. Wherein a cell is transformed by the genetic construct, a whole organism may be regenerated from a single transformed cell, using any method known to those skilled in the art.

By "transfect" is meant that the introduced nucleic acid molecule is introduced into said cell without integration into the cell's genome.

By "transform" is meant that the introduced nucleic acid molecule or genetic construct comprising same or a fragment thereof comprising the chimeric gene sequence is stably integrated into the genome of the cell.

Means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al. 1985), microinjection of DNA (Crossway et al., 1986), microparticle bombardment of tissue explants or cells (Christou et al, 1988; Sanford, 1987), vacuum-infiltration of tissue with nucleic acid, or in the case of plants, T-DNA-mediated transfer from Agrobacterium to the plant tissue as described essentially by An et al. (1985), Herrera-Estrella et al. (1983a, 1983b, 1985), Schroeder et al (1993), Molvig et al (1997), or as described in the accompanying Examples.

For microparticle bombardment of cells, a microparticle is propelled into a cell to produce a transformed cell. Any suitable biolistic cell transformation methodology and apparatus, including that exemplified herein can be used in performing the present invention. Exemplary apparatus and procedures are disclosed by Stomp et al. (U.S. Pat. No. 5,122,466) and Sanford and Wolf (U.S. Pat. No. 4,945,050). When using biolistic transformation procedures, the genetic construct may incorporate a plasmid capable of replicating in the cell to be transformed.

Examples of microparticles suitable for use in such systems include 1 to 5 $\mu$m gold spheres. The DNA construct may be deposited on the microparticle by any suitable technique, such as by precipitation.

Alternatively, wherein the cell is derived from a multi-cellular organism and where relevant technology is available, a whole organism may be regenerated from the transformed cell, in accordance with procedures well known in the art.

Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristermatic centres.

The term "embryogenesis", as used herein, means a process by which shoots and roots develop together in a concerted fashion (not sequentially), whether from somatic cells or gametes.

The regenerated transformed plants may be propagated by a variety of means to ensure that the introduced chimeric gene is maintained in the population, such as by clonal propagation or classical breeding techniques. For example, a first generation (or T1) transformed plant may be selfed or crossed to another T1 plant and homozygous second generation (or T2) transformants selected. In the case of woody crops which are not readily selfed to make homozygous plants, clonal derivatives of primary transformants will need to be crossed to each other to produce homozygous T2 plants. The T2 plant may then be fiber propagated through classical breeding techniques.

The regenerated transformed organisms contemplated herein may take a variety of forms. For example, they may be chimeras of transformed cells and non-transformed cells; clonal transformants (e.g., all cells transformed to contain the expression cassette); grafts of transformed and untransformed tissues (e.g., in plants, a transformed root stock grafted to an untransformed scion).

The plants that are produced according to the inventive method possess are of high economic and nutritional value compared to otherwise isogenic non-transformed plants. For example, increased protein content and/or oil content and/or a decreased content of anti-nutritional factors of seeds, including seeds of peas and chickpeas, increases their food quality for humans.

Additionally, plant seeds containing significantly increased protein are preferred ingredients in feed mixes containing other seeds rich in starch, for example unmodified cereals. Protein content is a major determinant of quality and value in cereals. High-protein cereals possess increased value in many applications and, in particular high-protein, wheat, rice, barley, maize, oats and sorghum may attract a price premium as improved ingredients in animal feeds. The protein of legume seeds is naturally low in the nutritionally-essential amino acids, methionine and cysteine. Accordingly, the present invention affords the additional benefit of increased sulfurous amino acid content, in addition to increased protein levels per se.

Additionally, the fibre in lupin seeds is not readily utilised by non-ruminant animals and, as a consequence, reduced seed fibre increases the nutritive value of lupin seed for non-ruminant animals. In particular, the soluble fraction of NSP (including oligosaccharides) in lupins is anti-nutritional for pigs and poultry. Accordingly, a reduction in the soluble NSP content of lupin seeds (as exemplified herein) further increases the nutritive value of lupins for non-ruminants. This modification may increase the market share of domestic lupins for feed formulations that currently use imported soybean meal.

Moreover, the modified plants produced according to the inventive method may have greater applicability than their parental counterparts as protein sources in aquaculture feeds. Plant protein must be concentrated for use in aquaculture feeds because prawns and fish cannot metabolise plant fibre. High protein grains would be preferred base materials for the preparation of these concentrates. Furthermore, prawns have a high nutritional requirement for arginine. As well as having increased total protein, transgenic peas and chickpeas expressing SSA have been enriched in arginine compared to non-transformed otherwise isogenic lines and, as a consequence, the modified seeds derived therefrom have high nutritive value for prawns. Nutritional supplements are particularly difficult to apply in aquaculture because of the problems associated with their delivery in a liquid medium.

Accordingly, a second aspect of the invention clearly extends to the transformed plants produced according to the inventive method described herein and the progeny plants and plant parts, such as the leaves, stems, roots, shoots, seed, tubers and flowers, amongst others derived therefrom which comprise at least one copy of the introduced chimeric gene in an expressible format.

In a particularly preferred embodiment, this aspect of the invention extends to the propagating material or storage organs derived from the transformed plants that are produced according to the inventive method and to the progeny plants derived from said propagating material, the only requirement being that said propagating material and/or storage organs and/or progeny plants comprise at least one copy of the introduced chimeric gene in an expressible format.

The present invention clearly extends to the use of genetic constructs designed to facilitate the introduction of the chimeric gene in a plant cell.

Accordingly, a third aspect of the invention provides a genetic construct which at least comprises a chimeric gene comprising a structural gene encoding a sulfur-rich peptide, oligopeptide, polypeptide, protein or enzyme placed in operable connection with a promoter sequence.

Wherein the structural gene does not possess its own transcription termination sequence, it is preferred that the genetic construct further comprises a terminator sequence placed downstream of the coding region of the structural gene.

The genetic construct of the invention preferably further comprises other genetic sequences to facilitate its maintenance in a prokaryotic or eukaryotic cell and/or its integration into the genome of the plant.

For example, the genetic constructs of the invention may further include an origin of replication sequence which is required for replication in a specific cell type, for example a bacterial cell, when said genetic construct is required to be maintained as an episomal genetic element (eg. plasmid or cosmid molecule) in said cell.

Preferred origins of replication include, but are not limited to, the fl-ori and colE1 origins of replication.

The genetic construct may further comprise a selectable marker gene or genes that are functional in a cell into which said genetic construct is introduced.

As used herein, the term "selectable marker gene" includes any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene such as the phosphinothricin acetyltransferase (PAT) gene (bar), neomycin phosphotransferase gene (nptII), hygromycin resistance gene (hph), β-glucutonidase (uidA) gene, chloramphenicol acetyltransferase (CAT) gene and luciferase gene, amongst others.

Those skilled in the an will be aware that the genetic construct may further include genes in addition to those specifically referred to herein. The present invention further contemplates the incorporation of genes which may influence the sulfur, carbon or nitrogen metabolism of plants into the genetic constructs described herein.

Those skilled in the art will also be aware of the advantage of having the chimeric gene cosegregate with the selectable marker gene or other introduced genes. This may achieved advantageously by having both gene "cassettes" located on the same gene construct such that they are closely linked, to prevent recombination therebetween occurring at a high frequency.

Alternatively, the chimeric gene and the selectable marker gene or other gene cassettes may be contained on separate genetic constructs and co-transferred to the plant tissue, in which case it is necessary to select for the presence of both the selectable marker gene and the chimeric gene containing the genetic sequences encoding the sulfur-rich protein.

Further features of the present invention are more fully described in the accompanying Figures and Examples. It is to be understood, however, that this detailed description is included solely for the purposes of exemplifying the present invention, and should not be understood in any way as a restriction on the broad description of the invention as described above.

EXAMPLE 1

Transgenic Lupins Containing SSA

Figure 1:
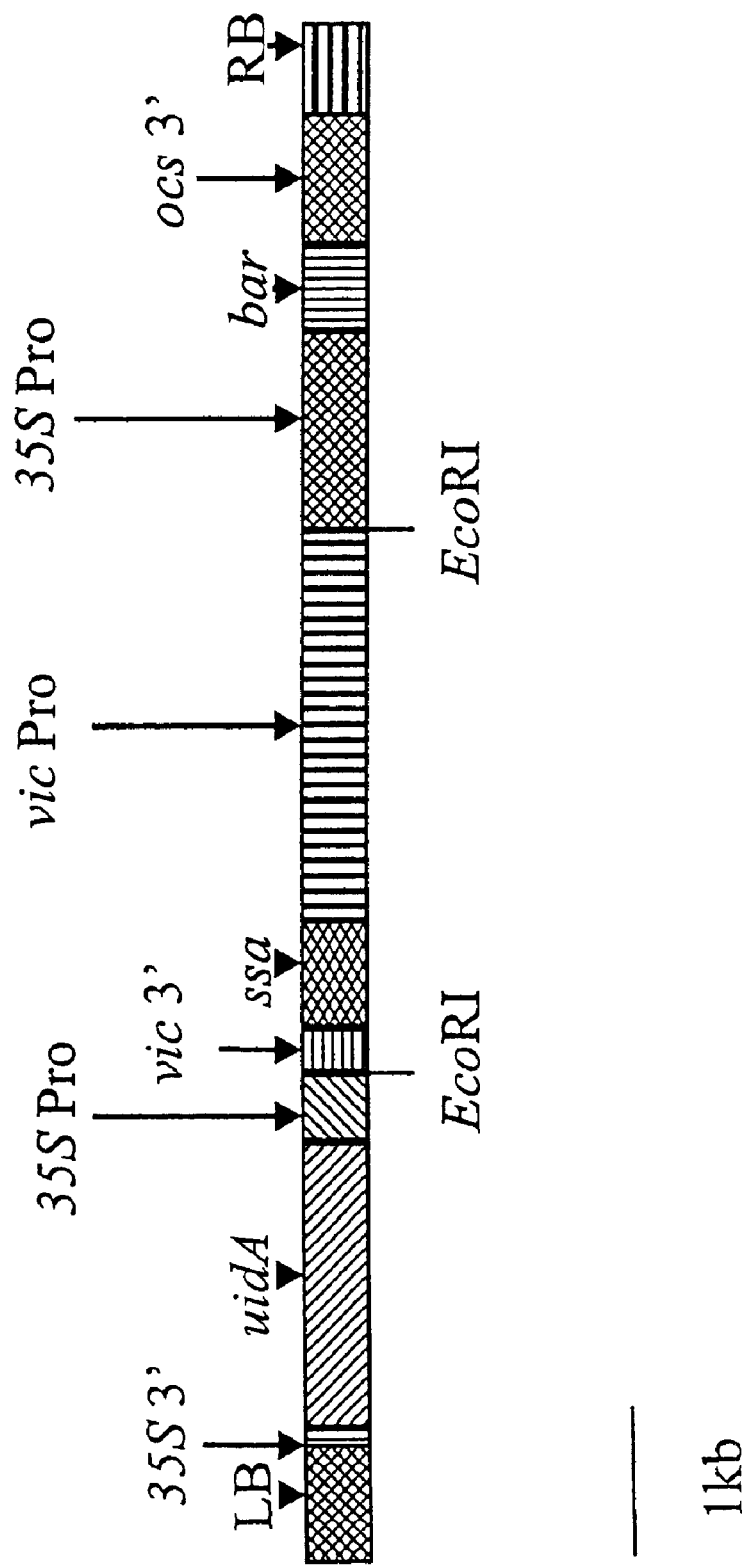
FIG. 1 is a diagrammatic representation of a genetic construct that comprises a chimeric gene encoding SSA which has been transferred to lupins, peas and chickpeas. The genetic construct contains three chimeric genes as follows.

Transgenic lupin seeds which contained SSA and which had elevated methionine content and enhanced nutritive value for rats have been produced by Agrobacterium-mediated transformation using the chimeric gene of FIG. 1 (Molvig et al., 1997). In addition to the expected increase in sulfur amino acid content of seed protein, it has been found that transgenic lupin seeds containing SSA have altered fibre composition compared to seeds of the parental lupin variety grown under essentially identical conditions (Table 1). The change in fibre composition was unexpected and unpredictable. An unexpected change in oil content and composition was also achieved by the expression of SSA in transgenic lines (Tables 1 and 2).

TABLE 1

Fibre and oil content (% dry matter) of wild type lupins and transgenic lupins containing SSA

| PARAMETER ASSAYED | [1]WILD TYPE CONTROL | [1]SSA TRANSGENIC LINE 55–38 |
|---|---|---|
| [2]Soluble NSP | 14.4 | 10.9 |
| Insol. NSP | 27.3 | 26 |
| [3]Total NSP | 41.7 | 36.9 |
| Lignin | 0.9 | 1.1 |
| [4]Total dietary fibre | 42.6 | 38 |
| Total oil | 5.0 | 6.2 |

[1]The wild type control seed and the transgenic seed (line 55–38, which is the transgenic line described in Molvig et al., 1997) were grown in green houses under the same conditions.
[2]NSP, Non-starch polysaccharide
[3]Total NSP is the sum of soluble and insoluble NSP
[4]Total dietary fibre is the sum of total NSP and lignin

TABLE 2

Oil composition [% (w/w) total fatty acids] of wild-type lupins and transgenic lupins containing SSA

| FATTY ACID | WILD-TYPE CONTROL | SSA-CONTAINING LINE 55–38 |
|---|---|---|
| myristic acid (C14:0) | 0.26 | 0.24 |
| palmitic acid (C16:0) | 13.39 | 13.10 |
| stearic acid (C18:0) | 6.55 | 8.17 |
| oleic acid (C18:1) | 34.97 | 38.22 |
| linoleic acid (C18:2) | 36.77 | 33.94 |
| linolenic acid (C18:3) | 5.49 | 4.02 |
| arachidic acid (C20:0) | 0.89 | 0.88 |
| gadoleic acid (C20:1) | 0.22 | 0.20 |
| behenic acid (C22:0) | 1.25 | 1.10 |
| erucic acid (C22:1) | 0.08 | 0.00 |
| lignoceric acid (C24:0) | 0.16 | 0.14 |

EXAMPLE 2

Transgenic Peas Containing SSA

The SSA gene was transferred to peas by Agrobacterium-mediated transformation according to Schroeder et al (1993) using the chimeric gene of FIG. 1, and instead of having significantly increased proportions of sulfur amino acids, the transgenic seeds had approximately 30% (up to 50%) more total seed protein than seeds of the parental, wild type plants grown under the same conditions in the glasshouse. As well as having increased protein, the transgenic seeds also bad reduced starch content relative to control seeds. Table 3 shows that pea seeds of several transgenic lines, derived from two different cultivars (the garden pea, cultivar Greenfeast and the field pea, cultivar Laura) contained more nitrogen and less starch than controls. Seed nitrogen is mostly in the form of protein, therefore, it can be assumed that increased seed nitrogen equates to increased seed protein. This assumption was tested directly by using precipitation with tri-chloroacetic acid (TCA) to measure the protein content of glasshouse-grown wild type and transgenic peas (Table 4). The results showed that the increase in seed nitrogen reflected an increase in seed protein.

Western blotting was used to confirm the presence of the sulfur-rich SSA in the transgenic pea seeds at a level equal to approximately 2% of total seed protein. X-ray fluorescence spectrometer analysis revealed that the organic sulfur content of transgenic pea seeds was increased by 21.1%. This increase was of similar magnitude to the increase in total seed nitrogen (26.3%, Table 4). therefore the seed protein was not enriched with respect to the sulfur-containing amino acids, methionine and cysteine.

As shown in Table 4, transformed *Pisum sativum* Cv. Laura seeds further have reduced total fatty acid content and increased fibre content in their seeds, in contrast the observed phenotype for lupin seeds expressing the ssa gene.

Determination of the amino acid composition of wild type pea seeds and transgenic pea seeds containing SSA confirmed that the amounts of all the amino acids had increased in seed of the transgenic line (Table 5). The levels of most amino acids, including methionine and cysteine had increased to similar extents. The increases in valise and isoleucine were less than the average change (which was about 30%) and the increase in arginine was greater than the average change, therefore the transgenic seeds were somewhat lower in their proportions of valine and isoleucine and higher in their proportion of arginine than their wild type counterparts.

TABLE 3

Seed nitrogen and starch composition (% dry matter) of wild type and transgenic *Pisum sativum* containing SSA

| Transformed lines of *P. sativum* Cv. Greenfeast | Nitrogen content (duplicate samples) | Starch content |
|---|---|---|
| line 115–14 | 6.26 | |
| | 6.13 | 30.0 |
| line 136–27 | 5.7 | |
| | 5.5 | 34.0 |
| line 133–87 | 4.61 | |
| | 5.26 | 33.0 |
| line 133–48 | 5.28 | |
| | 5.71 | 31.0 |
| line 133–54 | 4.3 | |
| | 6.22 | 31.0 |
| line 133–97 | 4.83 | |
| | 5.14 | 29.0 |
| line 133–77 | 5.26 | |
| | 4.77 | 33.0 |
| line 133–30 | 4.9 | |
| | 5.14 | 30.0 |
| mean (transformed lines) | 5.3 | 31.4 |
| Untransformed Greenfeast Control | 4.05 | 35.0 |
| | 4.34 | 36.0 |
| mean (untransformed control) | 4.2 | 35.5 |
| Change relative to control plants | +27% | −12% |
| line 816–77 | 4.78 | |
| | 4.45 | 47.0 |
| line 809–100 | 5.55 | |
| | 4.8 | 48.0 |
| line 800–27 | 5.14 | |
| | 5.8 | 46.0 |
| mean (transformed lines) | 5.09 | 47.0 |
| Untransformed Laura Control | 3.3 | 54.0 |
| | 3.36 | 53.0 |
| mean (untransformed control) | 3.33 | 53.5 |
| Change (transformed minus control) relative to control plants | +53% | −12% |

TABLE 4

Seed nitrogen, oil and crude fibre content (% dry matter) of seeds derived from wild-type and transformed *Pisum sativum* Cv. Laura containing SSA

| Plant Line | Total Seed Nitrogen | TCA-insoluble nitrogen | Oil content | Crude Fibre |
|---|---|---|---|---|
| Untransformed | 3.95 | 3.30 | 1.4 | 3.3 |
| SSA-transformed | 4.99 | 4.33 | 1.1 | 4.6 |
| change relative to control | +26.3% | +31.3% | −21.5% | +39.4% |

TABLE 5

Seed amino acid content of wild type untransformed and transformed SSA-containing *Pisum sativum*

| Amino acid | Wild type (mg/grain seed) | Transgenic (mg/grain seed) | % increase in transgenic line relative to control |
|---|---|---|---|
| aspartic acid | 21.3 | 28.6 | 34 |
| threonine | 7.9 | 10.55 | 34 |
| serine | 9.45 | 13.21 | 40 |
| glutamic acid | 34.6 | 45.59 | 32 |
| proline | 7.97 | 10.12 | 27 |
| glycine | 9.0 | 11.28 | 25 |
| alanine | 9.07 | 11.55 | 27 |
| valine | 9.94 | 11.22 | 13 |
| isoleucine | 9.43 | 10.42 | 10 |

TABLE 5-continued

Seed amino acid content of wild type untransformed and transformed SSA-containing *Pisum sativum*

| Amino acid | Wild type (mg/grain seed) | Transgenic (mg/grain seed) | % increase in transgenic line relative to control |
|---|---|---|---|
| leucine | 14.13 | 17.8 | 21 |
| lysine | 14.94 | 19.04 | 27 |
| arginine | 13.27 | 30.96 | 133 |
| cysteine | 2.57 | 3.57 | 39 |
| methionine | 2.13 | 2.81 | 32 |

In addition to an increase in total seed protein, transgenic pea seeds containing SSA had reduced levels of the endogenous, sulfur-rich, anti-nutritional proteins, trypsin inhibitor and chymotrypsin inhibitor. The levels of these inhibitors were measured by quantifying the inhibitory effects of total protein extracts from wild type or transgenic peas on the activity of trypsin or chymotrypsin in in vitro assays (Tables 6 & 7). Transgenic peas had 65% of the level of trypsin inhibitor in wild type seeds and 37% of the level of chymotrypsin inhibitor in wild type seeds.

TABLE 6

Seed trypsin inhibitor content of wild type untransformed and transformed SSA-containing *Pisum sativum*

| Plant extract | Trypsin activity (TAME units/min) | Trypsin inhibition by plant extract (%) | Inhibition by transgenic as % of inhibition by wild type |
|---|---|---|---|
| none (trypsin alone) | 70.08 | | |
| untransformed[1] | 56.41 | 20.33 | |
| transformed[2] | 61.42 | 13.24 | 65.13 |

[1] 4 mg of total protein extracted from wild type pea seed flour added to trypsin sample
[2] 4 mg of total protein extracted from transgenic pea seed flour added to trypsin sample

TABLE 7

Seed chymotrypsin inhibitor content of wild type untransformed and transformed SSA-containing *Pisum sativum*

| Plant extract | Chymotrypsin activity (OD units/min) | Chymotrypsin inhibition by plant extract (%) | Inhibition by transgenic as % of inhibition by wild type |
|---|---|---|---|
| none (chymotrypsin alone) | 12.17 | | |
| untransformed[1] | 9.82 | 19.28 | |
| transformed[2] | 11.3 | 7.12 | 37 |

[1] 20 mg of total protein extracted from wild type pea seed flour added to chymotrypsin sample
[2] 20 mg of total protein extracted from transgenic pea seed flour added to chymotrypsin sample

EXAMPLE 3

Transgenic Chickpeas Containing SSA

Chickpea seeds of the desi type are surface sterilised for 1 minute in 70% (v/v) ethanol followed by 20 minute sterilisation in 20% (v/v) commercial bleach (Marvolinn, 50 g/L sodium hypochlorite). Seeds are then rinsed 3–4 times in sterile distilled water, and imbibed for 24 hours on filter paper moistened with sterile distilled water (6 mL $H_2O$ per 15 seeds) at 24° C. under fluorescent light with a 16 hour photoperiod.

Explants are prepared by removing the seed coat, longitudinally bisecting the embryonic axis and then removing the root 2–3 mm from root tip. Therefore, each explant consists of one cotyledon attached to half of the embryonic axis.

Explants are collected in liquid MS medium (Murashige and Skoog, 1962), without hormones, until all seeds are dissected. The MS liquid is then replaced with an overnight culture of *Agrobacterium tumefaciens*, containing the plasmid pBSF16 (Molvig et al 1997). After a 30 minute incubation, explants are removed and plated with the cut surface facing down on cocultivation medium at a density of 30–40 explants per 100 mm diameter petri dish, The cocultivation medium is modified B5 medium (Gamborg et al, 1968) containing 20 g/L sucrose, 1 mg/L NAA, 1 mg/L BAP, 10 mM MES, solidified with 0.8% w/v Sigma agar and pH adjusted to 5.8. Coniferyl alcohol (100 uM) is added as a filter-sterilised solution to medium, previously autoclaved and cooled. The explants are cultured at $24^+/1°$ C. for 3 days in 16:8 hr light regime.

After cocultivation, the explants are washed thoroughly in 3–4 rinses of sterile water and blotted on sterile filter paper before plating on the first regeneration/section medium. This medium (MS-BKN) consists of MS salts, 30 g/L sucrose, 0.5 mg/L each of BAP and kinetin, 0.05 mg/L NAA, 10 mM MES, and solidified with 8 g/L Sigma agar and pH 5.8. To the cooled, autoclaved medium, 5 mg/L phosphinothricin (Technical Grade, a gift from Hoechst Ltd, Australia) is added for selection of transformed cells and 150 mg/L Timentin (Smithkline Beecham, Dandenong, Australia) to control Agrobacterium growth. Explants are plated on this medium at a density of 9 per 100×25 mm petri dish for two weeks.

After two weeks culture, the cotyledon is removed from the regenerating explants and the clump of shoots transferred to MS-BK medium (similar to MS-BKN but without NAA), in 65×80 mm polycarbonate screw top jars at a density of 5 shoot clumps per jar. Selection on 5 mg/L PPT is continued in all media until the rooting stage and Timentin is included in all media. Shoots surviving selection for two weeks on this medium are then transferred to MS-BK 0.1 medium (the level of BAP and kinetin are lowered to 0.1 mg/L). Regeneration and selection is continued on this medium, with subcultures every 2 weeks, until surviving shoots are 25–50 mm high. Actively growing shoots are removed from the shoot clump and roots induced on B5 medium (Gamborg et al 1968) containing 20 g/L sucrose, 8 g/L sigma agar, 1 mg/L BA at pH 5.8. Rooted plantlets are transferred to soil in the glasshouse with an aluminium foil-covered polycarbonate jar inverted over the plant for the first few weeks until they become acclimatised.

The chimeric SSA gene was transferred to desi type chickpeas, cultivar Semsen, by Agrobacterium-mediated transformation as described above, using the chimeric gene of FIG. 1. Transgenic seeds were produced having approximately 30% more total protein (TCA-insoluble nitrogen) than seeds of the parental, wild type plants grown under the same conditions in the glasshouse (Table 8). As well as having increased protein, the transgenic seeds had reduced starch content relative to control seeds.

TABLE 8

Seed nitrogen content (% dry matter) of wild type (untransformed)
and transformed chick peas containing SSA.

| Plant line | Total seed nitrogen | TCA-insoluble seed nitrogen |
|---|---|---|
| Semsen control | 2.88 | 2.3 |
| SSA transgenic | 3.91 | 3.0 |
| change relative to control | +35.8% | +31.8% |

Transgenic chickpea seeds contained SSA at a level equal to approximately 5% of total seed protein. X-ray fluorescence spectrometer analysis revealed that the organic sulfur content of transgenic chickpea seeds was increased by 30.8%. This increase was of similar magnitude to the increase in total seed nitrogen (35.8%, Table 8). therefore the seed protein was not enriched with respect to the sulfur-containing amino acids, methionine and cysteine. Determination of the amino acid composition of wild type chickpea seeds and transgenic chickpea seeds containing SSA confirmed that the amounts of all the amino acids had increased in seed of the transgenic line (Table 9). The levels of most amino acids had increased to similar extents (about 25%). The increase in cysteine was less than the average change and the increase in methionine was greater than the average change, but the change in the two combined (30% for cys+met) was about the same as the average change (25%).

Thus, although the transgenic chickpea seeds did contain more sulfur amino acids than control seeds, they did not have higher proportions of total sulfur amino acids than control seeds. This was similar to what had been observed in transgenic peas. Transgenic chickpea seeds were also somewhat richer in arginine than control chickpea seeds.

TABLE 9

Amino acid content (mg/gram seed) of wild type chickpea seeds
and transgenic chick pea seeds containing SSA

| Amino acid | Wild type | Transgenic | % increase in transgenic relative to untransformed |
|---|---|---|---|
| aspartic acid | 19.3 | 24.2 | 25 |
| threonine | 6.9 | 8.0 | 16 |
| serine | 9.7 | 12.4 | 28 |
| glutamic acid | 28.2 | 36.4 | 29 |
| proline | 8.2 | 9.7 | 18 |
| glycine | 7.0 | 8.5 | 21 |
| alanine | 7.4 | 9.1 | 23 |
| valine | 8.3 | 1.03 | 24 |
| isoleucine | 7.9 | 9.9 | 25 |
| leucine | 13.4 | 16.8 | 25 |
| tyrosine | 5.4 | 6.5 | 20 |
| phenylalanine | 1.01 | 1.31 | 30 |
| lysine | 12.1 | 14.7 | 21 |
| arginine | 15.3 | 23.0 | 50 |
| cysteine | 3.4 | 3.7 | 9 |
| methionine | 3.0 | 4.6 | 53 |
| cys + met | 6.4 | 8.3 | 30 |

In addition to an increase in total seed protein, chickpea seeds containing SSA had reduced levels of the endogenous, sulfur-rich, anti-nutritional proteins, trypsin inhibitor and chymotrypsin inhibitor. The levels of these inhibitors were measured by quantifying the inhibitory effects of total protein extracts from wild type or transgenic chickpeas on the activity of trypsin or chymotrypsin in in vitro assays (Tables 10 & 11). Transgenic chickpeas had 49% of the level of trypsin inhibitor in wild type seeds and 44% of the level of chymotrypsin inhibitor in wild type seeds.

TABLE 10

Trypsin inhibitor content of wild type chickpea seeds
and transgenic chickpea seeds containing SSA

| Plant extract | Trypsin activity (TAME units/min) | Trypsin inhibition by plant extract (%) | Inhibition by transgenic as % of inhibition by wild type |
|---|---|---|---|
| none (trypsin alone) | 207 | | |
| untransformed[1] | 98.5 | 52.4 | |
| transformed[2] | 153.8 | 25.7 | 49 |

[1] 6 mg of total protein extracted from wild type chickpea seed flour added to trypsin sample
[2] 6 mg of total protein extracted from transgenic chickpea seed flour added to trypsin sample

TABLE 11

Seed chymotrypsin inhibitor content of wild type untransformed
and transformed SSA-containing chickpeas

| Plant extract | Chymotrypsin activity (OD units/min) | Chymotrypsin inhibition by plant extract (%) | Inhibition by transgenic as % of inhibition by wild type |
|---|---|---|---|
| none | 14.94 | | |
| untransformed[1] | 9.91 | 33.7 | |
| transformed[2] | 12.72 | 14.86 | 44.1 |

[1] 12 mg of protein extracted from wild type chickpea seed flour added to chymotrypsin sample.
[2] 12 mg of protein extracted from transgenic chickpea seed flour added to chymotrypsin sample.

EXAMPLE 4

Transgenic Rice Containing SSA

Chimeric SSA genes designated LT10 and LT11 (FIG. 2) were transferred to Oryza sativa Cv. Taipei in conjunction with a chimeric selectable marker gene (FIG. 3) by microparticle bombardment, essentially according to the method of Upadhyaya et al (1996), which is based on the method published earlier by Li et al (1993), which is incorporated herein by way of reference.

Briefly, gold particles (8–10 mg of 1μ and 5μ particles) were sterilized in 100 μl of absolute ethanol and collected by centrifugation at 10,000 rpm for 10 sec. The gold particles were re-suspended in 100 μl of sterile double-distilled water and again collected. The procedure was repeated and the particles resuspended in 100 μl sterile water. Plasmid DNA (5 μg, at a 1:4 molar ratio of chimeric selectable marker gene and either LT10 or LT11) was mixed with 50 ul of the gold particle suspension and 20 ul of 100 mM spermidine. Then 50 ul of 2.5 M $CaCl_2$ was added dropwise and the suspension mixed for 1–2 min and incubated at room temperature for 10 min. The DNA-coated gold particles were collected by centrifugation and resuspended in 50 ul of cold absolute ethanol. The thoroughly resuspended gold particles (6–8 μl) were placed in a macrocarrier and allowed to dry.

Approximately 60–100 secondary calli of 1–2mm in diameter were assembled in the centre of NB media plates containing osmotin (Mannitol and Sorbitol) 4 hr prior to microparticle bombardment. The calli were bombarded with the DNA-coated gold particles under the following conditions: Helium pressure, 1100 psi; Chamber vacuum, 26 in. Hg; Gap between Rupture disk and Macrocarrier, 20 mm; Gap between Macrocarier and target sample, 60 mm.

The bombarded rice calli were transferred to NH30 media the following day and incubated for 2–3 weeks until hygromycin-resistance was established. The resistant clusters were transferred to NH50 media for a further 2–3 weeks, after which time the resistant calli were transferred to pre-regeneration media (PRH50) for a further 7–12 days. The resistant calli were finally transferred to regeneration media (RNH50) for 3–6 weeks until plantlets developed. The plantlets were transferred to ½ MSH50 media until roots developed. Fully regenerated plants were ported out.

The transgenic rice plants were assayed to determine total protein content and SSA gene expression. Total protein as measured by seed nitrogen was determined according to Kjeldhal. The presence of SSA in the seed of transformed rice lines was assayed by western blotting.

Data are presented in Table 12, wherein lines designated by the numeric indicator "63" are transformed with the LT10 chimeric gene set forth in FIG. 2 and the lines designated by the numeric indicator "64" are transformed with the LT11 chimeric gene set forth in FIG. 2.

As shown in Table 12, transgenic rice plants expressing the SSA gene with the C-terminal KDEL extension under the control of either the Bx17 or the JAN808 promoter sequence accumulate higher levels of seed protein than do the seeds of otherwise isogenic non-transformed rice lines. The level of total seed nitrogen, expressed as a percentage of total dry matter in the seeds of transformed plants was approximately 41.8% higher than for non-transformed plants in the case of plants comprising the LT10 chimeric gene (the JAN808 promoter). For plants comprising the LT11 chimeric gene (i.e. the Bx17 promoter), the level of total seed nitrogen, expressed as a percentage of total dry matter in the seeds of transformed plants was approximately 56.8% higher than for non-transformed plants

TABLE 12

Correlation between expression of SSA and increased grain nitrogen content of rice

| SAMPLE | SEED NITROGEN (% dry matter) | SSA LEVEL (+/−) |
|---|---|---|
| 63-8 (1) | 1.43 | + |
| 63-8 (2) | 1.63 | + |
| 63-28 (1) | 1.16 | + |
| 63-28 (2) | 1.57 | + |
| 63-36 (1) | 1.43 | + |
| 63-36 (2) | 1.14 | + |
| 63-74 (1) | 1.30 | + |
| 63-74 (2) | 1.80 | + |
| 64-6 (2) | 1.98 | + |
| 64-8 (1) | 1.46 | + |
| 64-8 (2) | 1.63 | + |
| 64-11 (1) | 1.62 | + |
| 64-15 (1) | 1.58 | + |
| 64-15 (2) | 1.58 | + |
| 64-19 (1) | 1.31 | + |
| 64-19 (2) | 1.28 | + |
| 64-65 (1) | 1.23 | + |
| 64-85 (1) | 170 | + |
| 64-85 (2) | 1.72 | Not sufficient sample |
| 64-86 (2) | 1.67 | + |
| 64-90 (1) | 1.66 | + |
| 64-90 (2) | 1.75 | + |
| Non-transformed rice | 1.01 | − |

References

1. Altenbach, S. B., Kuo, C.-C., Staraci, L. C., Pearson, K. W., Wainwright, C., Georgescu, A., and Townsend, J. (1992). *Plant Mol. Biol.* 18: 235–245.
2. An et al. (1985) *EMBO J.* 4:277–284.
3. Armstrong, C. L., Peterson, W. L., Buchholz, W. G., Bowen, B. A. Sulc, S. L. (1990), *Plant Cell Reports* 9: 335–339.
4. Ausubel, F. M., Brent, R., Kingston, R E, Moore, D. D., Seidman, J. G., Smith, J. A., and Struhl, K. (1987). In: Current Protocols in Molecular Biology. Wiley Interscience (ISBN 047150338).
5. Blagrove, R. J., Gillespie, P. J., and Randall, P. J. (1976). *Aust. J. Plant Physiol.* 3: 173–184.
6. Chandler, P. M., Spencer, D., Randall, P. J., and Higgns, T. J. V. (1984). *Plant Physiol.* 75; 651–65.
7. Christou, P., McCabe, D. E., and Swain, W. F. (1988). *Plant Physiol* 87: 671–674.
8. Crossway et al. (1986) *Mol. Gen. Genet.* 202:179–185.
9. Fromm et al. (1985) *Proc. Natl. Acad. Sci. (USA)* 82:5824–5828.
10. Gamborg, O. L., Miller, R. A., Ojima, K. (1968) *Exp. Cell Res.* 50:151–158.
11. Herrera-Estela et al. (1983a) *Nature* 303: 209–213.
12. Herrera-Estella et al. (1983b) *EMBO J.* 2: 987–995.
13. Herrera-Estella et al. (1985) In: Plant Genetic Engineering, Cambridge University Press, New York, pp 63–93.
14. Jung, R., Tarczynski, M. C., Martino-Catt, S., Townsend, J., and Beach, L. (1996). Poster 37 at the Workshop on Sulfur Metabolism Apr. 9–13 1996, Newcastle upon Tyne, UK.
15. Kortt, A. A., Caldwell, J. B., Lilley, G. G. and Heggins, T. J. V. (1991). *Eur. J. Biochem.* 195:329–334.
16. Krens, F. A., Molendijk, L., Wulllems, G. J. and Schilperoort, R. A. (1982). *Nature* 296: 72–74.
17. Li, L. Qu, R. De Koshko, A Fauquet, C and Beachy, R N (1993) *Plant Cell Reports* 12: 250–255.
18. McPherson, M. J., Quirke, P., and Taylor, G. R. (1991) In: PCR: A Practical Approach. (series editors, D. Rickwood and B. D. Hames) IRL Press Limited, Oxford. pp1–253.
19. Molvig, L., Tabe, L. M., Eggum, B. O., Moore, A. E., Craig, S., Spencer, D., and Higgins, T. J. V. (1997). *Proc. Natl. Acad. Sc. USA* 94: 8393–8398.
20. Muntz, K., Christov, V., Jung, R., Saalbach, G., Saalbach, I., Waddell, D., Pickardt, T., and Schieder, O. (1997). In: Sulfur metabolism in higher plants. Molecular, ecophysiological and nutritional aspects, (Cram, W. J., De Kok, L. J., Stulen, I., Brunold, C., and Rennenberg, H. eds.) pp. 71–86, Leiden, Backhuys Publishers.
21. Murashige, T. and Skoog, F. (1962) *Physiol. Plantarum* 15:473–497.
22. Paszkowski et al. (1984) *EMBO J.* 3:2717–2722.
23. Saalbach, I., Pickardt, T., Waddell, D. R., Hillmer, S., Schnieder, O., and Muntz, K. (1995). *Euphytica* 85: 181–192.
24. Sambrook, J., Fritsch, E. F., and Maniatis, T. (1989) In: Molecular Cloning, a Laboratory Manual 2nd Edition, Cold Spring Harbor N.Y.: Cold Spring Harbor Laboratory Press.
25. Sanford, J. C., Klein, T. M., Wolf, E. D., and Allen, N. (1987). *Particulate Science and Technology* 5: 27–37.
26. Schroeder, H. E., Schotz, A. H., Wardley-Richardson, T. Spencer, D. and Higgins, T. J. (1993) *Plant Physiol.* 101:751–757.
27. Townsend, J. A. and Thomas, L. A. (1994). *J. Cell. Biochem. Suppl.* 18A: Abstract X1-014.
28. Upadhyaya, N M, Ramm, K. Yang, M Kositratana, W Waterhouse, P M (1996) Rice ragged stunt virus synthetic resistance genes and japonica rice transformation. In: Rice Genetics III (ed. G S Khush) IRRI. pp 773–779.

What is claimed is:

1. A method of modifying the content or composition, or content and composition, of a metabolite in the seed of a plant comprising:
   (i) introducing into a plant a chimeric gene comprising a nucleotide sequence encoding a sunflower seed albumin protein placed operably in connection with a promoter sequence capable of conferring expression in the seed wherein the nucleotide sequence is expessed in the seed; and
   (ii) determining the content or composition, or content and composition, of a metabolite in the seed, said metabolite selected from the group consisting of fatty acid, starch, soluble non-starch polysaccharide, insoluble non-starch polysaccharide, fibre arid total protein nitrogen,
   wherein the plant has a modified content or composition, or content and composition, of a metabolite in the seed thereof, as compared to a plant in which said chimeric gene is not expressed, and
   wherein the plant is wheat, oats, maize, barley, rice, sorghum, millet, rye, safflower, sunflower, soybean, pea, bean, lentil, or chickpea.

2. The method according to claim 1 wherein the total protein nitrogen content is increased.

3. The method according to claim 1 wherein the fibre content or composition is modified.

4. The method according to claim 1 wherein the fatty acid content is increased or decreased.

5. The method according to claim 1 wherein the plant is a dicotyledonous plant.

6. The method according to claim 5 wherein the dicotyledonous plant is a pea or chickpea plant.

7. The method according to claim 1 wherein the promoter sequence comprise the pea vicilin gene promoter sequence.

8. The method according to claim 1 wherein the plant is a monocotyledonous plant.

9. The method according to claim 8 wherein the monocotyledonous plant is a rice plant.

10. The method according to claim 1 wherein the promoter sequence is a *Triticum aestivum* HMW glutenin promoter sequence.

11. The method according to claim 1 further comprising the first steps of:
    (i) introducing the chimeric gene into a plant cell, tissue, organ or whole organism; and
    (ii) regenerating an intact plant therefrom.

12. A method of increasing the total protein nitrogen content of seeds of a plant, said method comprising
    (i) introducing into a plant a chimeric gene comprising a nucleotide sequence encoding a sunflower seed albumin protein placed operably in connection with a promoter sequence capable of conferring expression in the seeds, said nucleotide sequence also positioned upstream of a transcription termination sequence wherein the nucleotide sequence is expressed in the seeds; and
    (ii) determining the content of total protein nitrogen in the seeds;
    wherein the plant has an increased total protein nitrogen content in the seeds thereof as compared to the seeds of a plant which does not express the chimeric gene, and
    wherein the plant is wheat, oats, maize, barley, rice, sorghum, millet, rye, safflower, sunflower, soybean, pea, bean, lentil, or chickpea.

13. The method according to claim 12 wherein the promoter sequence is the pea vicilin gene promoter and the plant is a dicotyledonous plant.

14. The method according to claim 12 wherein the promoter sequence is the pea vicilin gene promoter sequence and the transcription termination sequence is a vicilin gene transcription terminator sequence.

15. The method according to claim 13 wherein the plant is pea or chickpea.

16. The method according to claim 12 wherein the promoter sequence is a wheat HMW glutenin gene promoter and the plant is a monocotyledonous plant.

17. The method according to claim 12 wherein the promoter sequence is the wheat HMW glutenin gene promoter and/or the transcription termination sequence NOS transcription terminator sequence.

18. The method according to claim 16 wherein the plant is a rice plant.

19. A method of increasing or decreasing fatty acid content of seeds of a plant, said method comprising:
    (i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds wherein the nucleotide sequence is expressed in the seeds; and
    (ii) determining the content of a fatty acid in the seed;
    wherein the plant has increased or decreased content of the fatty acid in the seeds thereof as compared to the seeds of a plant which does not express the chimeric gene, and
    wherein the plant is wheat, oats, maize, barley, rice, sorghum, millet, rye, safflower, sunflower, soybean, pea, bean, lentil, or chickpea.

20. The method according to claim 19 wherein the promoter sequence is the pea vicilin gene promoter and the plant is a dicotyledonous plant.

21. The method according to claim 19 wherein the promoter sequence is the pea vicilin gene promoter sequence and the transcription termination sequence is a vicilin gene transcription terminator sequence.

22. The method according to claim 20 wherein if the plant is pea the content of fatty acids in the seeds is decreased.

23. A method of modifying the fatty acid composition of seeds of a plant, said method comprising
    (i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and
    (ii) determining the fatty acid composition of the seeds; and
    (iii) wherein the plant has a modified fatty acid composition in the seeds thereof, as compared to seeds of a plant in which the chimeric gene is not expressed, and
    wherein the plant is wheat, oats, maize, barley, rice, sorghum, millet, rye, safflower, sunflower, soybean, pea, bean, lentil, or chickpea.

24. The method according to claim 23 wherein the promoter sequence is the pea vicilin gene promoter and the plant is a dicotyledonous plant.

25. The method according to claim 23 wherein the promoter sequence is the pea vicilin gene promoter sequence and the transcription termination sequence is a vicilin gene transcription terminator sequence.

26. The method according to claim 23 wherein the fatty acid is selected from the group consisting of: myristic acid, stearic acid, gadoleic acid, behenic acid, lignoceric acid, oleic acid, linoleic acid, linolenic acid and erucic acid.

27. A method of decreasing the starch content of seeds of a plant, said method comprising;
(i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and
(ii) determining the starch content of the seeds;
wherein the plant has a decreased starch content in the seeds thereof, as compared with seeds of a plant in which the chimeric gene is not expressed, and
wherein the plant is wheat, oats, maize, barley, rice, sorghum, millet, rye, safflower, sunflower, soybean, pea, bean, lentil, or chickpea.

28. The method according to claim 27 wherein the promoter sequence is the pea vicilin gene promoter and the plant is a dicotyledonous plant.

29. The method according to claim 27 wherein the promoter sequence is the pea vicilin gene promoter sequence and the transcription termination sequence is a vicilin gene transcription terminator sequence.

30. The method according to claim 28 wherein the plant is a pea plant.

31. A method of increasing or decreasing the fibre content of seeds of a plant, said method comprising:
(i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and
(ii) determining the fibre content of the seeds;
wherein the plant has an increased or a decreased content of fibre in the seeds thereof, as compared with seeds of a plant which does not express said chimeric gene, and
wherein the plant is wheat, oats, maize, barley, rice, sorghum, millet, rye, safflower, sunflower, soybean, pea, bean, lentil, or chickpea.

32. The method according to claim 31 wherein the promoter sequence is the pea vicilin gene promoter and the plant is a dicotyledonous plant.

33. The method according to claim 31 wherein the promoter sequence is the pea vicilin gene promoter sequence and the transcription termination sequence is a vicilin gene transcription terminator sequence.

34. The method according to claim 32 wherein if the plant is a pea plant the content of fibre in the seed is increased.

35. A method of modifying the fibre composition of seeds of a plant, said method comprising:
(i) the step of introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and
(ii) determining the fibre composition of the seeds;
(iii) wherein the plant has a modified fibre composition in the seeds thereof, as compared with seeds of a plant in which the chimeric gene is not expressed, and
wherein the plant is wheat, oats, maize, barley, rice, sorghum, millet, rye, safflower, sunflower, soybean, pea, bean, lentil, or chickpea.

36. The method according to claim 35 wherein the promoter sequence is the pea vicilin gene promoter and the plant is a dicotyledonous plant.

37. The method according to claim 36 wherein the promoter sequence is the pea vicilin gene promoter sequence and the transcription termination sequence is a vicilin gene transcription terminator sequence.

38. The method according to claim 35 wherein the content of soluble non-starch polysaccharide, or the content of insoluble non-starch polysaccharide, or the content of both in the seed is decreased.

39. The method according to claim 35 wherein the content of lignin in the seed is increased.

40. The method according to any one of claim 12, 19, 23, 27, 31, or 35 further comprising the first steps of:
(i) introducing the chimeric gene into a plant cell, tissue, organ or whole organism; and
(ii) regenerating an intact plant therefrom.

41. The method of claim 1 wherein the total protein nitrogen content of the seed is increased.

42. The method of claim 1 wherein the fibre content of the seed is increased or decreased.

43. The method of claim 1 wherein the fibre composition of the seed is modified.

44. The method of claim 1 wherein the total starch content of the seed is decreased.

45. The method of claim 1 wherein the total fatty acid content of the seed is increased or decreased.

46. The method of claim 1 wherein the fatty acid composition of the seed is modified.

47. The method of claim 1 wherein the chimeric gene further comprises a promoter sequence which confers strong expression at least in the seeds of the plant.

48. The method according to claim 47 wherein the promoter is the pea vicilin promoter.

49. The method according to claim 47 wherein the promoter is the wheat HMW glutenin promoter.

50. The method of claim 47 wherein the chimeric gene further comprises a transcription terminator sequence placed downstream of the sequence encoding SSA.

51. The method of claim 50 wherein the transcription terminator sequence is the pea vicilin gene terminator sequence.

52. The method according to claim 1, wherein the content or composition, or content and composition, of more than one metabolite in the seed of the plant is modified.

53. A method of increasing the total protein nitrogen content of seeds of a plant, said method comprising:
(i) introducing into a plant a chimeric gene comprising a nucleotide sequence encoding a sunflower seed albumin protein placed operably in connection with a promoter sequence capable of conferring expression in said seeds, said nucleotide sequence also positioned upstream of a transcription termination sequence wherein the nucleotide sequence is expressed in the seed; and
(ii) determining whether the content of total protein nitrogen in the seeds of the plant is increased as compared to that of a plant in which the chimeric gene is not expressed, wherein the plant is wheat, oats, maize, barley, rice, sorghum, millet, rye, safflower, sunflower, soybean, pea, bean, lentil, or chickpea.

54. A method of increasing or decreasing the fatty acid content of seeds of a plant, said method comprising:

(i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds wherein the nucleotide sequence is expressed in the seeds; and (ii) determining whether the content of a fatty acid in the seeds of the plant is increased or decreased as compared to that of a plant in which the chimeric gene is not expressed, wherein the plant is wheat, oats, maize, barley, rice, sorghum, millet, rye, safflower, sunflower, soybean, pea, bean, lentil, or chickpea.

55. A method of modifying the fatty acid composition of seeds of a plant, said method comprising:

(i) introducing into a plant a chimeric gene that comprises a structral gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and (ii) determining whether the fatty acid composition of the seeds of the plant is modified as compared to that of a plant in which the chimeric gene is not expressed, wherein the plant is wheat, oats, maize, barley, rice, sorghum, millet, rye, safflower, sunflower, soybean, pea, bean, lentil, or chickpea.

56. A method of decreasing the starch content of seeds of a plant, said method comprising:

(i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and (ii) determining whether the starch content of the seeds of the plant is decreased as compared to that of a plant in which the chimeric gene is not expressed, wherein the plant is wheat, oats, maize, barley, rice, sorghum, millet, rye, safflower, sunflower, soybean, pea, bean, lentil, or chickpea.

57. A method of increasing or decreasing the fibre content of seeds of a plant, said method comprising:

(i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and (ii) determining whether the fibre content of the seeds of the plant is increased or decreased as compared to that of a plant in which the chimeric gene is not expressed, wherein the plant is wheat, oats, maize, barley, rice, sorghum, millet, rye, safflower, sunflower, soybean, pea, bean, lentil, or chickpea.

58. A method of modifying the fibre composition of seeds of a plant, said method comprising:

(i) introducing into a plant a chimeric gene that comprises a structural gene sequence encoding sunflower seed albumin (SSA) placed upstream of a transcription termination sequence and operably in connection with a promoter sequence capable of conferring expression on said structural gene in the seeds of said plant wherein the nucleotide sequence is expressed in the seeds; and (ii) determining whether the fibre composition of the seeds of the plant is modified as compared to that of a plant in which the chimeric gene is not expressed, wherein the plant is wheat, oats, maize, barley, rice, sorghum, millet, rye, safflower, sunflower, soybean, pea, bean, lentil, or chickpea.

59. The method according to claim 1, wherein the total protein nitrogen content of the seed of the plant is increased by at least 10%.

* * * * *